Jan. 27, 1976 R. S. MOORE Plant Pat. 3,826
MINIATURE ROSE PLANT
Filed Sept. 30, 1974
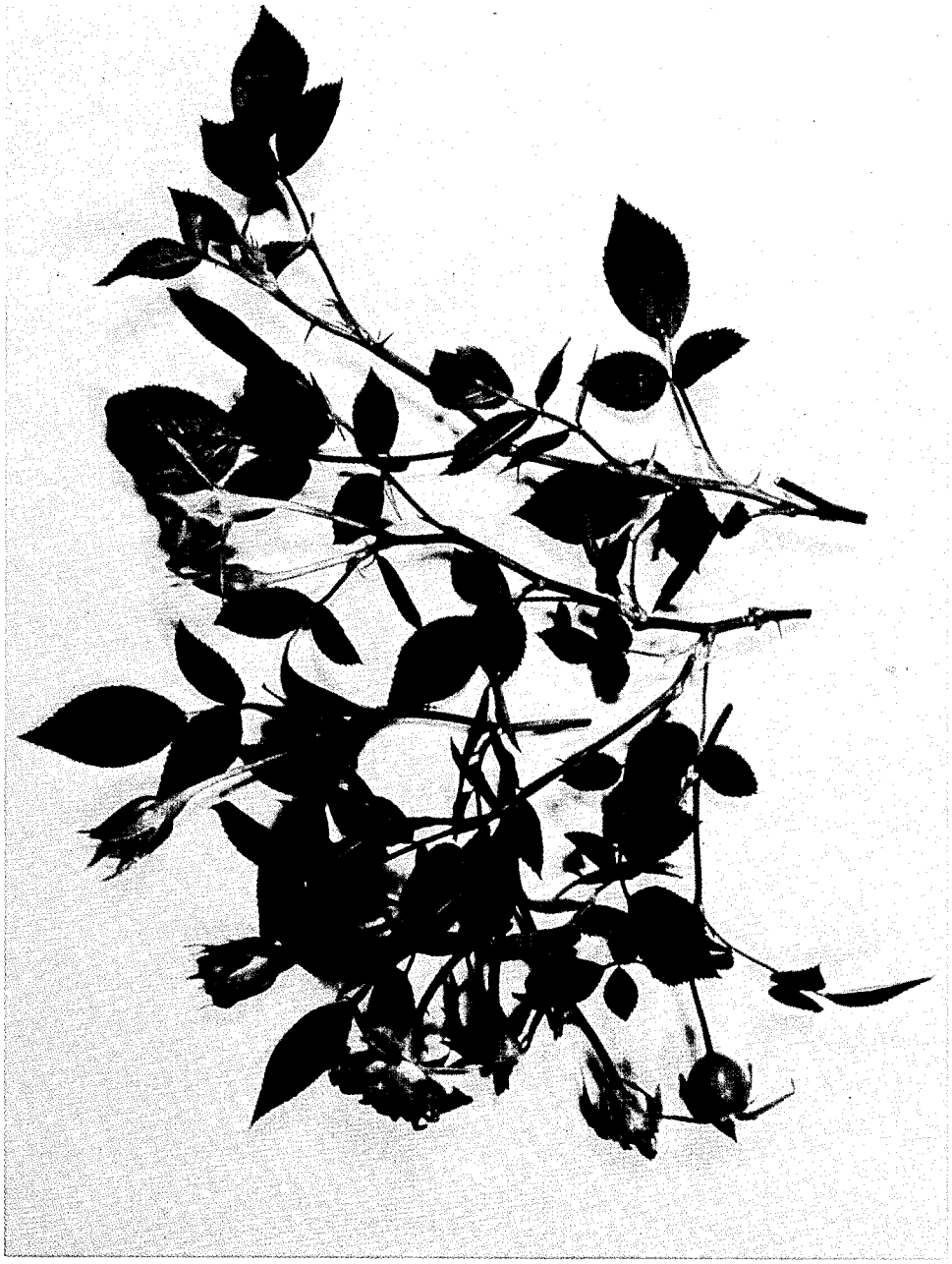

United States Patent

Plant Pat. 3,826

Patented Jan. 27, 1976

1

3,826

MINIATURE ROSE PLANT

Ralph S. Moore, 2519 E. Noble Ave., Visalia, Calif. 93277

Filed Sept. 30, 1974, Ser. No. 511,021

Int. Cl. A01h 5/00

U.S. Cl. Plt.—10 1 Claim

The present invention relates to a new and distinct variety of hardy, dwarf, bush type rose plant of the miniature class; the variety being primarily characterized—as to novelty—by bright orange-red buds and flowers which in general color effect are a glow red similar in color to Starina (Pat. No. 2646).

The variety is further characterized by:

An abundance of bloom, with flowers borne singly or several to the stem in loose clusters.

Sweet fragrance.

A plant which is vigorous, of rounded spreading shape and with semi-glossy, moderately small foliage with pointed leaflets; the buds and flowers being similar in form and size to the variety "Starina" (United States Plant Pat. No. 2,646); but less double. The plant, which has a normal height of 12 to 14 inches can easily be maintained at a lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between "Little Darling" (floribunda—Plant Pat. No. 1,581, expired) as the seed parent and "New Penny" (mininature—not patented) as the pollen parent.

Subsequent to origination of the variety I successfully asexually reproduced it, in my nursery located as aforesaid, by budding as well as by cuttings; the reproductions having run true in all respects.

The color photograph illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seedling; greenhouse; outdoors; cut flowers garden decoration; potted plant.

Class: Miniature.

Flowers: Continuity; Continuous—repeat bloom all season. Fragrance: moderate, sweet.

Flowers borne: Singly and several together (3 to 5) on strong, medium length stems.

Quantity of bloom: Abundant both outside and in greenhouse.

Bud: Peduncle—medium length; slender but sturdy; erect; medium green, sometimes tinted bronze; hairs—numerous soft, short. Before calyx breaks: size—small. Form: medium long; pointed; with a few foliaceous appendages and numerous tiny short hairs on surface of bud; with foliaceous parts extending beyond the tip of the bud equal to one-half or more of its length. Color—medium green, occasionally tinted with bronze. As calyx breaks: color—medium red. As first petal opens: same general color but more orange-red and showing whitish to light yellow tones near base of petal; size—small.

Bloom: Size when fully open—small, averaging about 1½". Petalage—double—20, arranged regularly. Form—slightly cupped at first, becoming more open in the center, with petals rolled loosely outward, and later

2 at maturity open with petals rolled loosely outward and downward. Edges of petals tend to fold back imparting a pointed effect.

Petals: Fairly thick; satiny both inside and outside. Shape—Outside petals—broad lanceolate with acute tip; intermediate—broad lanceloate with more rounded tip; inside—lanceolate with acute tip.

Color: Newly opened flower from a plant grown in plastic greenhouse (October 1970), Visalia, Calif.

*Outside petal:* Outside surface—near Delft Rose 020 with yellow area at base; inside surface—near Signal Red 719 with yellow at base.

*Intermediate petal:* Outside surface—near Delft Rose 020/1 with yellow at base; inside surface—near Signal Red 719 with bright yellow at base.

*Inner petal:* Outside surface—same as intermediate petal; inside surface—same as intermediate petal. General color effect newly opened flowers—bright orange-red color, similar to "Starina," but lighter, more orange-red color. Three days open—color less intense. Behavior—as flowers age petals may become lighter shade before dropping off. Spent petals drop off. Flower longevity (September 1974)—bush in garden or pot 4 to 5 days or longer. Cut flowers at living room temperature 4 to 6 days.

Reproductive organs:

Stamens: Abundant, arranged regularly about pistil.

Filament: Short; yellow.

Anthers: Well formed; yellow.

Pollen: Abundant; yellow.

Pistils: Average number.

Styles: Fairly even; short; bunched; color—red.

Stigma: Nearly white or pale yellow.

Ovaries: All enclosed in calyx.

Hips: Numerous; fairly large.

Sepals: Permanent; spear shaped; lightly recurved.

Seeds: Moderate number; do not germinate well.

Foliage:

Leaves—Compound of five leaflets; abundant; moderately small; leathtery; semi-glossy.

Leaflets—Shape: Lanceolate; apex acute; base acute or rounded acute. Margin serrate. Color: Normal green; new growth—reddish or tinted bronze (outdoors). Rachis: Medium strength; upper side has several tiny short prickles, grooved; under side sparsely thorny with few very tiny prickles. Stipules: Fairly long; medium width; medium length narrow points which may turn out at both more or less than 45 degrees.

Growth:

Habit—Dwarf; bushy; rounded; much branched.

Growth—Free; vigorous.

Canes—Medium; slender; sturdy.

Main stems: Color: dull green. Thorns: few; medium length; hooked slightly downward; color; brown or reddish-brown. Prickles—none. Hairs—none.

Branches—Color: medium green. Thorns: sparsely thorny; medium length; very slender; nearly straight; medium to short oval base. Prickles: none. Hairs: none.

New shoots—Color: medium green; often tinted red or bronze. Thorns: few to moderate; medium length; straight, greenish to reddish color; sharp points; base oval. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type, as illustrated and described, characterized by buds and flowers resembling the "Starina" (Plant Pat. No. 2,646) miniature rose in general form and color but with more open (less petals) flowers, the color being similar but of usually a brighter and lighter hue; the general color effect being orange-red; and further characterized by a plant which is of vigorous and compact growth, easy to propagate from cuttings, with medium small semi-glossy foliage, an abundance of bloom, with flowers borne singly or several to the stem in loose spray or cluster.

No references cited.

ROBERT E. BAGWILL, Primary Examiner